United States Patent [19]

Stelzer et al.

[11] Patent Number: 5,686,392
[45] Date of Patent: Nov. 11, 1997

[54] PROCESS FOR PREPARING SUBSTITUTED N-CARBAMOYL-TETRAZOLINONES

[75] Inventors: Uwe Stelzer, Leverkusen; Wolfgang Gau, Wuppertal; Karl-Julius Reubke, Köln, all of Germany

[73] Assignee: Bayer Aktiengesellschaft, Leverkusen, Germany

[21] Appl. No.: 595,088

[22] Filed: Feb. 1, 1996

[30] Foreign Application Priority Data

Feb. 8, 1995 [DE] Germany ............... 195 04 059.7

[51] Int. Cl.$^6$ ............................................. C07D 257/04
[52] U.S. Cl. .................................. 504/261; 548/251
[58] Field of Search ........................ 548/251; 504/261

[56] References Cited

U.S. PATENT DOCUMENTS

| | | | |
|---|---|---|---|
| 4,618,365 | 10/1986 | Covey et al. | 71/92 |
| 5,589,439 | 12/1996 | Goto et al. | 504/261 |
| 5,605,920 | 2/1997 | Goto et al. | 514/381 |

FOREIGN PATENT DOCUMENTS

| | | |
|---|---|---|
| 0 146 279 | 6/1985 | European Pat. Off. . |
| 0 202 929 | 11/1986 | European Pat. Off. . |
| 0 571 854 A1 | 12/1993 | European Pat. Off. . |
| 0 571 855 A1 | 12/1993 | European Pat. Off. . |
| 0 572 855 A1 | 12/1993 | European Pat. Off. . |
| 0 578 090 A3 | 1/1994 | European Pat. Off. . |
| 0 612 735 A1 | 8/1994 | European Pat. Off. . |
| 0 646 577 A1 | 4/1995 | European Pat. Off. . |

OTHER PUBLICATIONS

Chemical Abstracts, vol. 80, abstract no. 82829r, p. 391 (1974).
E. Lippmann, Z.Chemie, vol. 13, pp. 429–430 (1973).

*Primary Examiner*—Joseph McKane
*Assistant Examiner*—Richard S. Myers, Jr.
*Attorney, Agent, or Firm*—Sprung Kramer Schaefer & Briscoe

[57] ABSTRACT

The herbicidally active substituted N-carbamoyl-tetrazolinones of the formula (I)

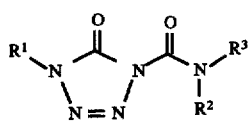

-continued

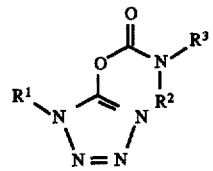

in which $R^1$ represents, inter alia, an (optionally substituted) phenyl radical, $R^2$ represents, inter alia, an alkyl radical, and $R^3$ represents, inter alia, a cycloalkyl radical, are obtained in very good yields and at high purity—i.e. free from the isomeric O-carbamoyloxytetrazoles (Ia)—by reacting tetrazolinones of the formula (II) with carbamoyl halides of the formula (III) (X=halogen)

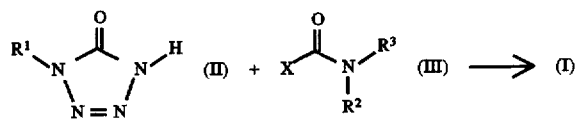

in the presence of an acid acceptor and in the presence of a diluent, at temperatures of between 0° C. and 200° C., and either isomerizing the O-carbamoylation product of the formula (Ia), which is formed under these circumstances as a byproduct, into the desired product of the formula (I) by heating, or else converting it by hydrolysis or alcoholysis into water-soluble, and thus readily separable, components (variable (a)).

Three variants (b), (c) and (d) which are closely related to this process (a) are also described:

Process variant (b) proceeds in analogy with (a) but via the (novel, isolated) metal salts (IIa) of the tetrazolinones (II). In variant (c), the isomer (Ia) is isomerized thermally, either in pure isolated form or mixed with (I), while, in variant (d), the (Ia) isomer is removed from (I)/(Ia) mixtures by means of hydrolysis or alcoholysis.

The novel intermediates (Ia) and (IIa) also belong, as such, to the subject-matter of the invention.

14 Claims, No Drawings

PROCESS FOR PREPARING SUBSTITUTED N-CARBAMOYL-TETRAZOLINONES

The invention relates to a novel process and to novel intermediates for preparing substituted N-carbamoyl-tetrazolinones, which are known to be compounds having herbicidal activity.

It is known that substituted carbamoyltetrazolinones are obtained when corresponding tetrazolinones are reacted with appropriate carbamic acid derivatives (cf. EP-A 146279, EP-A 202929, EP-A 578090 and EP-A 612735). When the preparation is carried out in this way, (undesired) O-carbamoylation is always observed in addition to the desired N-carbamoylation (with regard to the acylation of tetrazolinones, cf. Z. Chemie 13 (1973), 429–430, as well). As a consequence, products which are contaminated to a greater or lesser extent are obtained in many cases.

It has now been found that substituted N-carbamoyl-tetrazolinones of the general formula (I)

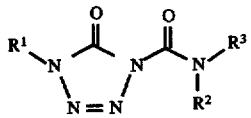
(I)

in which

R$^1$ represents alkyl, alkenyl, alkinyl, cycloalkyl, cycloalkylalkyl, aryl, arylalkyl, heterocyclyl or heterocyclylalkyl which are in each case optionally substituted, R$^2$ represents alkyl, alkenyl, alkinyl or alkoxy which are in each case optionally substituted, and R$^3$ represents alkyl, alkenyl, alkinyl, cycloalkyl, cycloalkylalkyl, aryl or arylalkyl which are in each case optionally substituted, or, together with R$^2$, represents alkanediyl, are obtained in very good yields and at high purity—i.e. free from the isomeric carbamoyloxytetrazoles (Ia)—when (a) Tetrazolinones of the general formula (II)

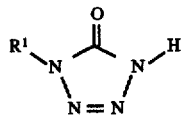
(II)

in which

R$^1$ has the abovementioned meaning, are reacted with carbamoyl halides of the general formula (III)

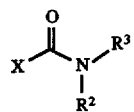
(III)

in which

R$^2$ and R$^3$ have the abovementioned meaning and

X represents halogen, in the presence of an acid acceptor and in the presence of a diluent, at temperatures of between 0° C. and 200° C., and the O-carbamoylation product of the formula (Ia)—below—which is formed under these circumstances as a byproduct is either isomerized by heating to form the desired product of the formula (II) or is converted by hydrolysis into water-soluble, and thus readily separable, components, or when (b) (isolated) tetrazolinone metal salts of the general formula (IIa)

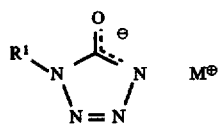
(IIa)

in which

R$^1$ has the abovementioned meaning, and

M represents an alkali metal equivalent, an alkaline earth metal equivalent or an earth metal equivalent, are reacted with carbamoyl halides of the general formula (III)

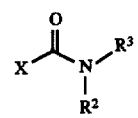
(III)

in which

R$^2$ and R$^3$ have the abovementioned meaning and

X represents halogen, in the presence of a diluent, at temperatures of 0° C. and 200° C., and the O-carbamoylation product of the formula (Ia)—see below—which arises under these circumstances as a byproduct is either isomerized by heating to form the desired product of the formula (I) or is converted by hydrolysis into water-soluble, and thus readily separable, components, or when (c) substituted carbamoyloxytetrazoles of the general formula (Ia)

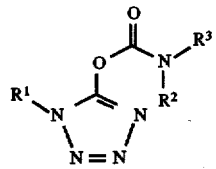
(Ia)

in which

R$^1$, R$^2$ and R$^3$ have the abovementioned meanings, which can also be present mixed with the compounds of the formula (I)

are isomerized to form the corresponding N-carbamoyl-tetrazolinones of the formula (I), where appropriate in the presence of a diluent and where appropriate in the presence of a reaction auxiliary, at temperatures of between 50° C. and 200° C., or when (d) substituted carbamoyloxytetrazoles of the general formula (Ia)

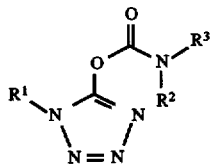
(Ia)

in which

R$^1$, R$^2$ and R$^3$ have the abovementioned meanings, which, as products of the reaction of compounds of the formula (II) and/or of compounds of the formula (IIa) with compounds of the formula (III), are present mixed with the compounds of the formula (I)

are reacted with water and/or an alcohol, in particular methanol, where appropriate in the presence of an inert organic solvent and where appropriate in the presence of a reaction auxiliary, at temperatures of between 10° C. and 150° C., and the products of the hydrolysis or the alcoholysis of the compounds of the formula (Ia) are separated off using customary methods.

Surprisingly, the N-carbamoyltetrazolinones of the formula (I) can be prepared by the novel process, in its four variants described above under (a), (b), (c) and (d), in what are for the most part substantially higher yields, and in markedly improved quality, as compared with the known state of the art, with it being possible, in particular, to minimize the proportion of the undesirable carbamoyloxytetrazoles of the formula (Ia).

The novel process, in all its variants, thus represents a valuable enrichment of the state of the art.

The novel process preferably relates to the preparation of compounds of the formula (I) in which $R^1$ represents alkyl which is optionally substituted by carboxyl, cyano, carbamoyl, halogen, $C_1$–$C_6$-alkoxy, $C_1$–$C_6$-alkylthio, $C_1$–$C_6$-alkylsulphinyl or $C_1$–$C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1$–$C_4$-alkyl or $C_1$–$C_4$-alkoxy-carbonyl and which in each case have from 3 to 8 carbon atoms in the cycloalkyl moiety and optionally from 1 to 4 carbon atoms in the alkyl moiety, or represents phenyl, naphthyl, phenyl-$C_1$–$C_4$-alkyl, naphthyl-$C_1$–$C_4$-alkyl, furyl, benzofuryl, tetrahydrofuryl, furylmethyl, tetrahydrofurylmethyl, thienyl, benzothienyl, tetrahydrothienyl, thienylmethyl, tetrahydrothienylmethyl, pyrrolyl, indolyl, oxazolyl, benzoxazolyl, oxazolylmethyl, isoxazolyl, isoxazolylmethyl, thiazolyl, benzothiazolyl, thiazolylmethyl, pyrazolyl, oxadiazolyl, oxadiazolylmethyl, thiadiazolyl, thiadiazolylmethyl, triazolyl, pyridyl, quinolinyl, isoquinolinyl, pyridylmethyl, pyrazinyl, pyridazinyl, pyrimidinyl, quinazolinyl, quinoxalinyl, pyrimidinylmethyl, triazinyl or triazinylmethyl which are in each case optionally substituted by carboxyl, cyano, carbamoyl, nitro, amino, hydroxyl or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonyl-amino, di-($C_1$–$C_4$-alkyl) aminosulphonyl, $C_1$–$C_4$-alkyl-carbonyl, $C_1$–$C_4$-alkyl-carbonylamino, $C_1$–$C_4$-alkoxy-carbonyl, di-($C_1$–$C_4$-alkyl-amino)-carbonyl, $C_1$–$C_4$-alkylenedioxy, phenyl or phenoxy (which are in each case optionally substituted by fluorine and/or chlorine), $R^2$ represents alkyl, alkenyl or alkinyl which are in each case optionally substituted by cyano or halogen and which in each case have up to 6 carbon atoms, and $R^3$ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1$–$C_4$-alkyl and which in each case have from 3 to 6 carbon atoms in the cycloalkyl moiety and optionally from 1 to 2 carbon atoms in the alkyl moiety, or represents phenyl or phenyl-$C_1$–$C_2$-alkyl, which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl or $C_1$–$C_4$-alkoxy-carbonyl (which are in each case optionally substituted by fluorine and/or chlorine), or, together with $R^2$, represents alkanediyl having from 2 to 6 carbon atoms.

The novel process relates, in particular, to the preparation of compounds of the formula (I) in which $R^1$ represents methyl, ethyl, n- or i-propyl, n-, i-, s- or t-butyl, n-, i- or s-pentyl, n-, i- or s-hexyl which are in each case optionally substituted by cyano, fluorine, chlorine, methoxy, ethoxy, methylthio, ethylthio, methylsulphinyl, ethylsulphinyl, methylsulphonyl or ethylsulphonyl, represents propenyl, butenyl, pentenyl, hexenyl, propinyl, butinyl, pentinyl or hexinyl which are in each case optionally substituted by cyano, fluorine, chlorine or bromine, represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine or bromine, or represents phenyl, benzyl, phenylethyl, furyl, tetrahydrofuryl, furylmethyl, tetrahydrofurylmethyl, thienyl, tetrahydrothienyl, thienylmethyl, tetrahydrothienylmethyl, oxazolyl, oxazolylmethyl, isoxazolyl, isoxazolylmethyl, thiazolyl, thiazolylmethyl, oxadiazolyl, oxadiazolylmethyl, thiadiazolyl, thiadiazolylmethyl, pyridyl, pyridylmethyl, pyrimidinyl, pyrimidinylmethyl, triazinyl or triazinylmethyl which are in each case optionally substituted by cyano, fluorine, chlorine or bromine, or by methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, dimethylaminosulphonyl, diethylaminosulphonyl, methylcarbonyl, ethylcarbonyl, n- or i-propylcarbonyl, methoxycarbonyl, ethoxycarbonyl, n- or i-propoxycarbonyl, dimethylaminocarbonyl, diethylaminocarbonyl, methylenedioxy or ethylenedioxy (which are in each case optionally substituted by fluorine and/or chlorine), $R^2$ represents methyl, ethyl, n- or i-propyl, n-, i- or s-butyl, propenyl, butenyl, propinyl or butinyl which are in each case optionally substituted by cyano, fluorine or chlorine, and $R^3$ represents methyl, ethyl, n- or i-propyl, n-, i- or s-butyl, propenyl, butenyl, propinyl or butinyl which are in each case optionally substituted by cyano, fluorine or chlorine, represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, bromine, methyl or ethyl, or represents phenyl, benzyl or phenylethyl which are in each case optionally substituted by cyano, fluorine, chlorine, methyl, ethyl, methoxy or ethoxy, or, together with $R^2$ and the adjacent N-atom, represents pyrrolidino, piperidino or morpholino.

The tetrazolinones which are to be used as starting compounds in the variant of the novel process described above under (a)—"process variant (a)"—are defined generally by the formula (II). In the compounds of the formula (II), $R^1$ preferably or in particular has that meaning which has already been indicated above, in the description of the compounds of the formula (I) which are to be prepared by the novel process, as being preferred or in particular preferred for $R^1$.

The starting compounds of the formula (II) are known and/or can be prepared by methods which are known per se (cf. J. Am. Chem. Soc. 81 (1959), 3076–3079; J. Org. Chem. 45 (1980), 5130–5136; EP-A 146279; EP-A 572855; EP-A 578090).

The carbamoyl halides to be used as starting compounds in process variant (a) and also in process variant (b) are defined generally by the formula (III). In the compounds of the formula (III), $R^2$ and $R^3$ preferably or in particular have that meaning which has already been indicated above, in the description of the compounds of the formula (I) which are to be prepared by the novel process, as being preferred or in particular preferred for $R^2$ and $R^3$, respectively; X preferably represents fluorine, chlorine or bromine, in particular chlorine.

The starting compounds of the formula (III) are known organic synthesis chemicals.

The tetrazolinone metal salts to be used as starting compounds in process variant (b) are defined generally by the formula (IIa). In the compounds of the formula (II), $R^1$ preferably or in particular has that meaning which has already been indicated above, in the description of the compounds of the formula (I) which are to be prepared by the novel process, as being preferred or in particular preferred for $R^1$; M preferably represents lithium, sodium or potassium, or represents a magnesium, calcium, barium or aluminium equivalent, and in particular represents sodium or potassium.

The tetrazolinone metal salts of the formula (IIa) have not yet been disclosed in the literature as isolated products; as novel compounds, they also belong to the subject-matter of the present application.

The novel tetrazolinone metal salts of the formula (IIa) are obtained when tetrazolinones of the general formula (II)

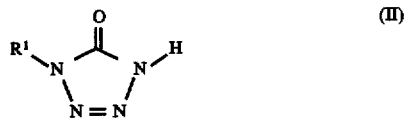

(II)

in which
$R^1$ has the abovementioned meaning, are reacted with alkali metal, alkaline earth metal or earth metal compounds of the general formula (IV)

M—Z (IV)

in which
M represents an alkali metal equivalent, alkaline earth metal equivalent or earth metal equivalent, preferably represents a lithium, sodium, potassium, magnesium, calcium, barium or aluminium equivalent, and in particular represents sodium or potassium, and Z represents hydroxyl, a carbonate equivalent, a hydrogen carbonate equivalent, or—preferably—an alcohol equivalent, preferably represents methoxy, ethoxy, n- or i-propoxy or n-, i-, s- or t-butoxy, and in particular represents methoxy or ethoxy, in the presence of a diluent, such as methanol, ethanol, n- or i-propanol or n-, i-, s- or t-butanol, at temperatures of between 0° C. and 150° C., preferably of between 20° C. and 120° C., and the diluent is then distilled off—preferably under reduced pressure.

The substituted carbamoyloxytetrazoles which are used as starting compounds in process variants (c) and (d) are defined generally by the formula (Ia). In the formula (Ia), $R^1$, $R^2$ and $R^3$ preferably or in particular have that meaning which has already been indicated above, in the description of the compounds of the formula (I) which are to be prepared by the novel process, as being preferred or in particular preferred for $R^1$, $R^2$ and $R^3$, respectively.

The carbamoyloxytetrazoles of the formula (Ia) have not previously been disclosed in the literature; as novel compounds, they also belong to the subject-matter of the present application. To a certain extent the compounds of formula (Ia) exhibit herbidical activity.

In general, the carbamoyloxytetrazoles of the formula (Ia) arise in mixtures together with N-carbamoyl-tetrazolinones of the formula (I) in association with the reaction of tetrazolinones of the formula (II), or their salts, with carbamoyl chlorides of the formula (III) at low or moderately elevated temperatures. They can be reacted in these mixtures in accordance with process variants (c) and (d) or else isolated in advance from these mixtures using customary methods.

The novel process variant (a) is carried out in the presence of an appropriate acid acceptor. All the customary inorganic or organic bases are suitable for use as this acid acceptor. These bases include, for example, alkali metal- or alkaline earth metal-hydrides, hydroxides, amides, alcoholates, acetates, carbonates or hydrogen carbonates, such as lithium, sodium, potassium or calcium hydride, lithium, sodium or potassium amide, sodium or potassium methoxide, sodium or potassium ethoxide, sodium or potassium propoxide, aluminium isopropoxide, sodium or potassium tert-butoxide, sodium or potassium hydroxide, sodium, potassium or calcium acetate, sodium, potassium or calcium carbonate or sodium or potassium hydrogen carbonate, and also basic organic nitrogen compounds, such as trimethylamine, triethylamine, tripropylamine, tributylamine, ethyl-diisopropylamine, N,N-dimethylcyclohexylamine, dicyclohexylamine, ethyl-dicyclohexylamine, N,N-dimethylaniline, N,N-dimethylbenzylamine, pyridine, 2-methyl-, 3-methyl- and 4-methyl-pyridine, 2,4-dimethyl-, 2,6-dimethyl-, 3,4-dimethyl- and 3,5-dimethyl-pyridine, 5-ethyl-2-methyl-pyridine, N-methylpiperidine, 4-dimethylaminopyridine, diazabicyclooctane (DABCO), diazabicyclononene (DBN) or diazabicycloundecene (DBU).

Lithium carbonate, sodium carbonate, potassium carbonate or calcium carbonate, or the corresponding hydrogen carbonates, are preferably employed as acid acceptors in the novel process variant (a).

The customary inert organic solvents are suitable for use as diluents for carrying out the novel process variant (a). These solvents include, in particular, aliphatic, alicyclic or aromatic, optionally halogenated, hydrocarbons, such as pentane, hexane, heptane, petroleum ether, ligroin, benzine, benzene, toluene, xylene, chlorobenzene, dichlorobenzene, cyclohexane, methylcyclohexane, dichloromethane, chloroform or tetrachloromethane; ethers, such as diethyl ether, diisopropyl ether, t-butyl methyl ether, t-pentyl methyl ether, dioxane, tetrahydrofuran, ethylene glycol dimethyl ether, ethylene glycol diethyl ether, diethylene glycol dimethyl ether or diethylene glycol diethyl ether; ketones, such as acetone, butanone or methyl isobutyl ketone; nitriles, such as acetonitrile, propionitrile, butyronitrile or benzonitrile; amides, such as N,N-dimethylformamide, N,N-dimethylacetamide, N-methylformanilide, N-methylpyrrolidone or hexamethylphosphoric triamide; esters, such as methyl, ethyl, n- or i-propyl or n-, i- or s-butyl acetate; sulphoxides, such as dimethyl sulphoxide; alcohols, such as methanol, ethanol, n- or i-propanol, n-, i-, s- or t-butanol, ethylene glycol monomethyl ether, ethylene glycol monoethyl ether, diethylene glycol monomethyl ether or diethylene glycol monoethyl ether.

Aprotic polar solvents, such as t-pentyl methyl ether, ethylene glycol dimethyl ether, ethylene glycol diethyl ether, methyl isobutyl ketone, acetonitrile, propionitrile, butyronitrile, ethyl acetate, propyl acetate and butyl acetate are preferably employed as diluents in the novel process variant (a).

When carrying out the novel process variant (a), the reaction temperatures can be varied within a relatively wide range. In general, the variant is carried out using temperatures of between 0° C. and 200° C., preferably temperatures of between 10° C. and 80° C., in particular of between 20° C. and 60° C., in the initial phase and then preferably of between 50° C. and 150° C., in particular of between 70° C. and 130° C.

In general, the novel process variant (a) is carried out under standard pressure. However, it is also possible to carry it out under elevated or reduced pressure—in general between 0.1 bar and 10 bar.

In order to carry out the novel process variant (a) for preparing the compounds of the formula (I), from 0.9 to 1.5 mol, preferably from 1.0 to 1.2 mol, of carbamoyl halide of the formula (III) and from 1.0 to 1.5 mol, preferably from 1.0 to 1.2 mol, of acid acceptor are generally employed per mole of tetrazolinone of the formula (II).

In a preferred embodiment of the novel process variant (a), a tetrazolinone of the formula (II) is mixed with an acid acceptor and a diluent in the lower range of the abovementioned temperature interval, and the carbamoyl halide of the formula (III) is then added to this mixture. The reaction mixture is then maintained in the upper range of the abovementioned temperature interval until the end of the reaction or the rearrangement (in general for one or more hours, usually from about 1 to 25 hours).

The subsequent steps for isolating the products of the formula (I) may expediently be carried out as follows:

After the mixture has been cooled down, water is added to it and the organic phase is separated off; where appropriate, the mixture is extracted once again, and the solvent is distilled off from the combined organic phases. The residue is heated for several hours with water and, where appropriate, an organic solvent, such as methanol or toluene, where appropriate in the presence of a reaction auxiliary, such as hydrochloric acid. The organic phase is then separated off—where appropriate after adding an organic solvent, such as toluene, which is virtually immiscible with water; where appropriate the mixture is extracted once again and the combined organic phases are stirred together with a dilute aqueous solution of sodium hydroxide and then separated off, dried and filtered. After concentrating the residue is crystallized by digesting it with a suitable organic solvent, such as hexane, and the product is isolated by filtering it off with suction.

The novel process variant (b) is carried out in the presence of a diluent. In the main, the same diluents are suitable for use in this context as those which were mentioned above for the novel process variant (a).

Aprotic polar solvents, such as ethylene glycol dimethyl ether, ethylene glycol diethyl ether, methyl isobutyl ketone, acetonitrile, propionitrile, butyronitrile, ethyl acetate, propyl acetate and butyl acetate are preferably employed as diluents in the novel process variant (b) as well.

When carrying out the novel process variant (b), the reaction temperatures can be varied within a relatively wide range. In general, the variant is carried out at temperatures of between 0° C. and 200° C., preferably at temperatures of between 10° C. and 80° C., in particular of between 20° C. and 60° C., in the initial phase, and preferably of between 50° C. and 150° C., in particular of between 70° C. and 130° C., subsequently.

In general, the novel process variant (b) is carried out under standard pressure. However, it is also possible to carry it out under elevated or reduced pressure—in general between 0.1 bar and 10 bar.

In order to carry out the novel process variant (b) for preparing the compounds of the formula (I), from 0.9 to 1.5 mol, preferably from 1.0 to 1.2 mol, of carbamoyl halide of the formula (III) are generally employed per mol of tetrazolinone metal salt of the formula (IIa).

In a preferred embodiment of the novel process variant (b), a tetrazolinone metal salt of the formula (IIa) is prepared, in a preceding step, from a tetrazolinone of the formula (III) and an alkali metal compound, alkaline earth metal compound or earth metal compound of the formula (IV), and then isolated by distilling off the solvent. The product which is thus obtained is then taken up in one of the abovementioned inert diluents, and a carbamoyl halide of the formula (III) is added to this solution; the mixture is then kept for some time (in general from about 1 to 25 hours) in the upper range of the abovementioned temperature interval.

The working up can be carried out in accordance with customary methods, for example as described above for process variant (a).

Where appropriate, the novel process variant (c) is carried out in the presence of a diluent. In the main, the same diluents are suitable for use in this context as those which were mentioned above for the novel process variant (a). However, process variant (c) can also advantageously be carried out without using any diluent.

Where appropriate, process variant (c) is carried out in the presence of a reaction auxiliary. Reaction auxiliaries which preferably come into consideration in this context are basic organic nitrogen compounds, such as trimethylamine, triethylamine, tripropylamine, tributylamine, ethyldiisopropylamine, N,N-dimethylcyclohexylamine, dicyclohexylamine, ethyl-dicyclohexylamine, N,N-dimethylaniline, N,N-dimethyl-benzylamine, pyridine, 2-methyl-, 3-methyl- and 4-methyl-pyridine, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methylpiperidine, N,N-dimethylaminopyridine, diazabicyclooctane (DABCO), diazabicyclononene (DBN) or diazabicycloundecene (DBU). Pyridine and 4-dimethylamino-pyridine are in particular suitable for use as reaction auxiliaries in process variant (c). Besides, or instead of, these compounds, iodine or alkali metal iodides are also suitable for use as reaction auxiliaries.

When carrying out the novel process variant (c), the reaction temperatures can be varied within a relatively wide range. In general, temperatures of between 50° C. and 200° C., preferably of between 60° C. and 170° C., in particular of between 80° C. and 150° C., are employed.

In general, the novel process variant (c) is carried out under standard pressure. However, it is also possible to carry it out under elevated or reduced pressure—in general at between 0.1 bar and 10 bar.

In order to carry out process variant (c), the reaction components are generally mixed at room temperature and heated at the requisite reaction temperature until the reaction (isomerization) has come to a halt. Working-up can then take place in accordance with the above-described method (cf. variants (a) and (b)) and the product can be purified by recrystallization.

The novel process variant (d) is preferably carried out in the presence of an organic solvent. The solvents listed above in association with the description of process variant (a) are in the main suitable for use in this context.

The novel process variant (d) is preferably carried out in the presence of a suitable reaction auxiliary. All the customary inorganic or organic bases are suitable for use as such an auxiliary. These include, for example, alkali metal or alkaline earth metal hydrides, hydroxides, amides, alcoholates, acetates, carbonates or hydrogen carbonates, such as lithium, sodium, potassium or calcium hydride, lithium, sodium or potassium amide, sodium or potassium methoxide, sodium or potassium ethoxide, sodium or potassium propoxide, aluminium isopropoxide, sodium or potassium tert-butoxide, sodium or potassium hydroxide, ammonium hydroxide, sodium, potassium or calcium acetate, ammonium acetate, sodium, potassium or calcium carbonate, ammonium carbonate or sodium or potassium hydrogen carbonate, and also basic organic nitrogen compounds, such as trimethylamine, triethylamine, tripropylamine, tributylamine, ethyl-diisopropylamine, N,N-dimethylcyclohexylamine, dicyclohexylamine, ethyl-dicyclohexylamine, N,N-dimethylaniline, N,N-dimethylbenzylamine, pyridine, 2-methyl-, 3-methyl- or 4-methyl-pyridine, 2,4-dimethyl-, 2,6-dimethyl-, 3,4-dimethyl- and 3,5-dimethyl-pyridine, 5-ethyl-2-methyl-pyridine, N-methylpiperidine, 4-dimethylaminopyridine, diazabicyclooctane (DABCO), diazabicyclononene (DBN) or diazabicycloundecene (DBU).

Acids are also suitable for use as an alternative reaction auxiliary in process variant (d). These acids include inorganic acids or mineral acids, such as hydrochloric acid, sulphuric acid, phosphoric acid and nitric acid, and also organic acids, such as acetic acid, methanesulphonic acid, benzenesulphonic acid and p-toluenesulphonic acid.

Where appropriate, the novel process variant (d) can also be carried out in a two-phase system, such as water/toluene or water/dichloromethane, where appropriate in the presence of a suitable phase-transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyl-dimethyl-ammonium methyl sulphate, dimethyl-$C_{12}$/$C_{14}$-alkyl-benzylammonium chloride, dimethyl-$C_{12}$/$C_{14}$-alkyl-benzylammonium bromide, tetrabutylammonium hydroxide, trithylbenzylammonium chloride, methyltrioctylammonium chloride, trimethylbenzylammonium chloride, 15-crown-5, 18-crown-6 or tris-[2-(2-methoxyethoxy)-ethyl]-amine.

When carrying out the novel process variant (d), the reaction temperatures can be varied within a relatively wide range. In general, temperatures of between 10° C. and 150° C., preferably temperatures of between 20° C. and 120° C., in particular of between 25° C. and 100° C. are employed.

In general, the novel process variant (d) is carried out under standard pressure. However, it is also possible to carry it out under elevated or reduced pressure—in general between 0.1 bar and 10 bar.

In order to carry out process variant (d), the reaction components are generally mixed at room temperature and heated at the requisite reaction temperature until the reaction (hydrolysis or alcoholysis) is complete. Working-up can then take place in accordance with customary methods (cf. variants (a) and (b)).

The substituted N-carbamoyl-tetrazolinones of the formula (I) which can be prepared in accordance with the invention may be used as herbicides for controlling unwanted plant growth (cf. EP-A 146 279, EP-A 202 929, EP-A 571 854, EP-A 571 855, EP-A 572 855, EP-A 578 090 and EP-A 612 735).

PREPARATION EXAMPLES

Example 1

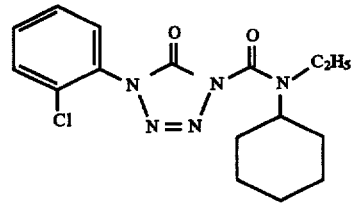

(A) Preparation of a compound of the formula (IIa):

A mixture consisting of 39.3 g (200 mmol) of 1-(2-chloro-phenyl)-1,4-dihydro-5H-tetrazol-5-one, 11.0 g (201 mmol) of sodium methoxide and 200 ml of methanol is heated under reflux for 4 hours. The solvent is then carefully distilled off in a water suction vacuum. The sodium salt of 1-(2-chloro-phenyl)-1,4-dihydro-5H-tetrazol-5-one is obtained in quantitative yield as a solid residue (melting point: 170° C. with decomposition), which can be subjected to further reaction in the same reaction vessel.

(B) Preparation of a compound of the formula (I) in accordance with process variant (b):

10.7 g (50 mmol) of the sodium salt of 1-(2-chloro-phenyl)-1,4-dihydro-5H-tetrazol-5-one are initially introduced in 100 ml of 1,2-dimethoxyethane, and a solution of 10.0 g (52.5 mmol) of N-cyclohexyl-N-ethyl-carbamoyl chloride in 10 ml of 1,2-dimethoxyethane is added at room temperature (approximately 20° C.). The mixture is then heated under reflux for approximately 17 hours. It is subsequently concentrated, after which the residue is shaken with ethyl acetate/water and the organic phase is separated off; the aqueous phase is subsequently extracted with ethyl acetate and the combined organic phases are dried with sodium sulphate and filtered. The filtrate is concentrated and the residue is heated under reflux for 17 hours together with a mixture consisting of 200 ml methanol and 50 ml of water, concentration then takes place once again. The residue is taken up in ethyl acetate, and this solution is stirred together with 50 ml of 1N sodium hydroxide solution. The phases are then separated and the aqueous phase is subsequently extracted with toluene; the organic phases are combined, dried with sodium sulphate and filtered. The filtrate is concentrated and the residue is recrystallized from hexane.

15.4 g (88% of theory) of 1-(2-chloro-phenyl)-4-(N-cyclohexyl-N-ethylaminocarbonyl)-1,4-dihydro-5H-tetrazol-5-one are obtained.

Under these circumstances, the corresponding (isomeric) O-carbamoylation product is no longer detectable with the customary analytical methods.

$^{15}$N-NMR (D7-DMF, ext. reference: nitromethane): −25.7, −32.2, −162.5, −176.4, −249 ppm.

Example 2

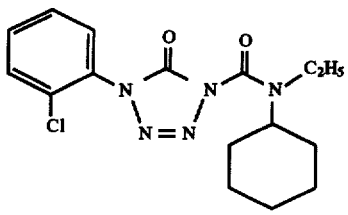

(A) Preparation of a compound of the formula (IIa):

A mixture consisting of 9.8 g (50 mmol) of 1-(2-chloro-phenyl)-1,4-dihydro-5H-tetrazol-5-one, 2.8 g (51 mmol) of sodium methoxide and 100 ml of methanol is heated under reflux for 2 hours. The solvent is then carefully distilled off in a water suction vacuum. The sodium salt of 1-(2-chloro-phenyl)-1,4-dihydro-5H-tetrazol-5-one is obtained in quantitative yield as a solid residue, which can be subjected to further reaction in the same reaction vessel.

(B) Preparation of a compound of the formula (I) in accordance with process variant (b):

The entire quantity of the sodium salt of 1-(2-chloro-phenyl)-1,4-dihydro-5H-tetrazol-5-one which was obtained in accordance with the above description is initially introduced in 100 ml of 1,2-dimethoxyethane, and a solution of 10.4 g (55 mmol) of N-cyclohexyl-N-ethyl-carbamoyl chloride in 10 ml of 1,2-dimethoxyethane is added at room temperature (approximately 20° C.). The mixture is then heated under reflux for approximately 17 hours. It is subsequently concentrated and the residue is heated under reflux for 9 hours together with a mixture consisting of 200 ml of methanol and 50 ml of water; concentration then takes place once again. The residue is taken up in toluene and this solution is stirred together with 50 ml of a 1N solution of sodium hydroxide. The phases are then separated, with the aqueous phase being subsequently extracted with toluene; the organic phases are combined, dried with sodium sulphate and filtered. The filtrate is concentrated and the residue is recrystallized from hexane.

15.2 g (87% of theory) of 1-(2-chloro-phenyl)-4-(N-cyclohexyl-N-ethylaminocarbonyl)-1,4-dihydro-5H-tetrazol-5-one are obtained.

Under these circumstances, the corresponding (isomeric) O-carbamoylation product is no longer detectable using customary analytical methods.

Example 3

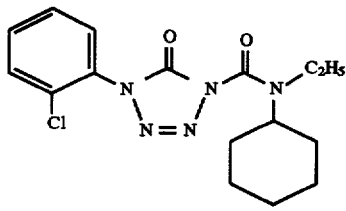

(in accordance with process variant (c)):

11.6 mg of a mixture consisting of 1-(2-chloro-phenyl)-4-(N-cyclohexyl-N-ethyl-aminocarbonyl)-1,4-dihydro-5H-tetrazol-5-one and the corresponding isomeric carbamoyloxytetrazole in a ratio by weight of 57:37 is slowly heated to approximately 170° C. Once this temperature has been reached, the heating is discontinued and a content determination is carried out. This indicates a content of 89% of 1-(2-chloro-phenyl)-4-(N-cyclohexyl-N-ethyl-aminocarbonyl)-1,4-dihydro-5H-tetrazol-5-one with the content of the corresponding isomeric carbamoyloxytetrazole now only being 2% The determination also indicates the additional presence of 2 components of unknown structure with a content in each case of 6%.

When the above-described pyrolytic isomerization is carried out after having added 0.01 ml of pyridine, the content of 1-(2-chloro-phenyl)-4-(N-cyclohexyl-N-ethyl-aminocarbonyl)-1,4-dihydro-5H-tetrazol-5-one is found to be 94%; while an unknown minor constituent is still detected, its content is now only 4% and no isomeric carbamoyloxytetrazole is found.

Example 4

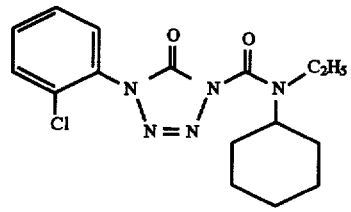

(in accordance with process variant (a)):

2.0 g of a mixture consisting of 1-(2-chloro-phenyl)-4-(N-cyclohexyl-N-ethyl-aminocarbonyl)-1,4-dihydro-5H-tetrazol-5-one and the corresponding isomeric carbamoyloxytetrazole in a ratio by weight of 1:1 are heated under reflux for 20 hours in a mixture consisting of 80 ml of methanol and 20 ml of water. The whole is then concentrated, and the residue is taken up in methylene chloride and this solution is shaken with 20 ml of a 1N solution of sodium hydroxide; the aqueous phase is subsequently extracted with methylene chloride and the combined organic phases are dried with sodium sulphate and filtered. The solvent is carefully distilled off from the filtrate in a water suction vacuum. 1-(2-Chloro-phenyl)-4-(N-cyclohexyl-N-ethyl-aminocarbonyl)-1,4-dihydro-5H-tetrazol-5-one is obtained in quantitative yield as a crystalline residue.

Example 5

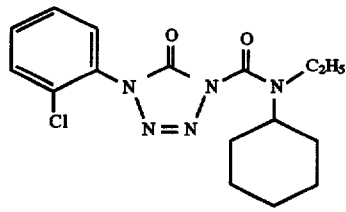

(in accordance with process variant (d)):

1.0 g of a mixture consisting of 1-(2-chloro-phenyl)-4-(N-cyclohexyl-N-ethyl-aminocarbonyl)-1,4-dihydro-5H-tetrazol-5-one and the corresponding isomeric carbamoyloxytetrazole in a ratio by weight of 1:1 is stirred, at approximately 20° C. for 17 hours, in a mixture consisting of 10 ml of toluene and 10 ml of 10% aqueous hydrochloric acid. The organic phase is then separated off and shaken with 10 ml of a 1N solution of sodium hydroxide; the aqueous phase is subsequently extracted with methylene chloride, and the combined organic phases are dried with sodium sulphate and filtered. The solvent is carefully distilled off from the filtrate in a water suction vacuum.

1-(2-Chloro-phenyl)-4-(N-cyclohexyl-N-ethyl-aminocarbonyl)-1,4-dihydro-5H-tetrazol-5-one is obtained in quantitative yield as a crystalline residue.

Example 6

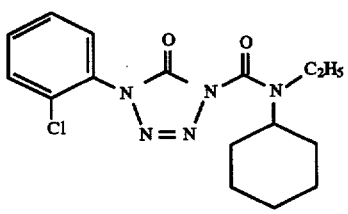

(in accordance with process variant (a)):

9.8 g (50 mmol) of 1-(2-chloro-phenyl)-1,4-dihydro-5H-tetrazol-5-one are initially introduced, together with 5.8 g (54 mmol) of sodium carbonate, in 100 ml of ethyl acetate, and 10.4 g (54 mmol) of N-cyclohexyl-N-ethyl-carbamoyl chloride in 20 ml of ethyl acetate are added. The mixture is heated under reflux for 16 hours and then, after having been cooled down to room temperature (approximately 20° C.), is shaken with water. The aqueous phase is then subsequently extracted with ethyl acetate. The organic phases are then combined and concentrated in a water suction vacuum. The residue is stirred, at 20° C. for 16 hours, together with 200 ml of toluene and 100 ml of 10% aqueous hydrochloric acid and, after the organic phase has been separated off, the aqueous phase is subsequently extracted with toluene. The combined organic phases are then stirred for 30 minutes together with 100 ml of a 1N solution of sodium hydroxide. The organic phase is then separated off and the aqueous phase is subsequently extracted with toluene. The combined organic phases are dried with sodium sulphate and filtered. The filtrate is concentrated in a water suction vacuum and the residue is recrystallized by digesting it with n-hexane.

16.0 g (purity: 96.4%, yield: 91.5% of theory) of 1-(2-chloro-phenyl)-4-(N-cyclohexyl-N-ethyl-aminocarbonyl)-1,4-dihydro-5H-tetrazol-5-one are obtained. Under these circumstances, the corresponding (isometric) O-carbamoylation product is no longer detectable using customary analytical methods.

Example 7

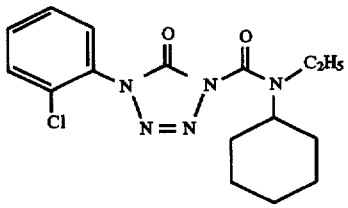

(in accordance with process variant (a)):

9.8 g (50 mmol) of 1-(2-chloro-phenyl)-1,4-dihydro-5H-tetrazol-5-one are initially introduced, together with 5.8 g (54 mmol) of sodium carbonate, in 100 ml of ethyl acetate, and 10.4 g (54 mmol) of N-cyclohexyl-N-ethyl-carbamoyl chloride in 20 ml of ethyl acetate are added. The mixture is heated under reflux for 16 hours and, after it has been cooled down to room temperature (approximately 20° C.), is shaken with water. The aqueous phase is then subsequently extracted with ethyl acetate. The organic phases are then combined and concentrated in a water suction vacuum. The residue is heated under reflux for approximately 20 hours together with 200 ml of methanol and 50 ml of water and this mixture is then concentrated. The residue is taken up in toluene and this solution is stirred up together with 100 ml of a 1N solution of sodium hydroxide. The subsequent working-up is carried out as described in Example 6.

15.2 g (purity: 96.4%, yield: 87% of theory) of 1-(2-chloro-phenyl)-4-(N-cyclohexyl-N-ethyl-amincarbonyl)-1,4-dihydro-5H-tetrazol-5-one are obtained.

Carbamoyloxytetrazoles of the formula (Ia):

Example (Ia-1)

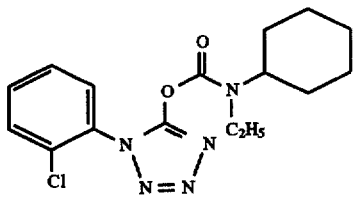

19.6 g (100 mmol) of 1-(2-chloro-phenyl)-1,4-dihydro-5H-tetrazol-5-one, 12.8 g (120 mmol) of sodium carbonate and 0.1 g of 4-dimethylamino-pyridine are initially introduced in 150 ml of toluene, and a solution of 22.8 g (120 mmol) of N-cyclohexyl-N-ethyl-carbamoyl chloride in 50 ml of toluene is added. The mixture is stirred at from 50° C. to 55° C. for 17 hours and then, after having been cooled down to room temperature (approximately 20° C.), is shaken with water. The aqueous phase is then subsequently extracted with ethyl acetate. After that, the organic phases are combined and concentrated in a water suction vacuum.

34 g (89% of theory) of a 1:1 mixture consisting of 1-(2-chloro-phenyl)-4-(N-cyclohexyl-N-ethyl-aminocarbonyl)-1,4-dihydro-5H-tetrazol-5-one and the corresponding isomeric carbamoyloxytetrazole are obtained.

The two isomers are resolved using customary methods. Thus, the carbamoyltetrazole of the above structural formula is obtained, for example, by chrormatography (preparative HPLC: Nucleosil 100 CN, 5 µm, 250×4 mm, heptane/t-butyl methyl ether, 80/20 by vol., isocratic, 2 ml/min, 3.5 µl injected, 0.3% solution in eluent) or by means of a so-called Craig distribution (200 steps, ethyl acetate/dimethylformamide, 3/7 by vol., and heptane/water, 7/3 by vol.).

$^{15}$N-NMR (D7-DMF, ext. reference: nitromethane): +11.9, −8.2, −73.0, −156.3, −271.1 ppm.

Comments on nomenclature:

The compound of the formula (I) described in Preparation Examples 1 to 7 can alternatively be rendered as follows:

according to CHEMICAL ABSTRACTS:
"4-(2-chlorophenyl)-4,5-dihydro-N-cyclohexyl-N-ethyl-5-oxo-1H-tetrazole-1-carboxamide";

according to the documents cited above with regard to the state of the art:
"1-(2-chlorophenyl)-4-(N-cyclohexyl-N-ethyl-carbamoyl)-5(4H)-tetrazolinone".

In an analogous manner, the starting compound of the formula (II) which was used is alternatively rendered as follows:

according to CHEMICAL ABSTRACTS:
"4-(2-chlorophenyl)-4,5-dihydro-5-oxo-1H-tetrazole";

according to the documents cited above with regard to the state of the art:
"1-(2-chlorophenyl)-5(4H)-tetrazolinone".

It will be appreciated that the instant specification and claims are set forth by way of illustration and not limitation, and that various modifications and changes may be made without departing from the spirit and scope of the present invention.

We claim:

1. A process for preparing a substituted N-carbamoyl-tetrazolinone of the formula

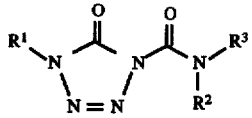  (I)

in which

R$^1$ represents alkyl which is optionally substituted by carboxyl, cyano, carbamoyl, halogen, C$_1$–C$_6$-alkoxy, C$_1$–C$_6$-alkylthio, C$_1$–C$_6$-alkylsulphinyl or C$_1$–C$_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, C$_1$–C$_4$-alkyl or C$_1$–C$_4$-alkoxy-carbonyl and which in each case have from 3 to 8 carbon atoms in the cycloalkyl moiety and optionally from 1 to 4 carbon atoms in the alkyl moiety, or represents phenyl, naphthyl, phenyl-C$_1$–C$_4$-alkyl, naphthyl-C$_1$–C$_4$-alkyl, furyl, benzofuryl, tetrahydrofuryl, furylmethyl, tetrahydrofurylmethyl, thienyl, benzothienyl, tetrahydrothienyl, thienylmethyl, tetrahydrothienylmethyl, pyrrolyl, indolyl, oxazolyl, benzoxazolyl, oxazolylmethyl, isoxazolyl, isoxazolylmethyl, thiazolyl, benzothiazolyl, thiazolylmethyl, pyrazolyl, oxadiazolyl, oxadiazolylmethyl, thiadiazolyl, thiadiazolylmethyl, triazolyl, pyridyl, quinolinyl, isoquinolinyl, pyridylmethyl, pyrazinyl, pyridazinyl, pyrimidinyl, quinazolinyl, quinoxalinyl, pyrimidinylmethyl, triazinyl or triazinylmethyl which are in each case optionally substituted by carboxyl, cyano, carbamoyl, nitro, amino, hydroxyl or halogen, or by C$_1$–C$_4$-alkyl, C$_1$–C$_4$-alkoxy, C$_1$–C$_4$-alkylthio, C$_1$–C$_4$-alkylsulphinyl, C$_1$–C$_4$-alkylsulphonyl, di-(C$_1$–C$_4$-alkyl)amino, C$_1$–C$_4$-alkylsulphonylamino, di-(C$_1$–C$_4$-alkyl) aminosulphonyl, C$_1$–C$_4$-alkyl-carbonyl, C$_1$–C$_4$-alkyl-carbonylamino, C$_1$–C$_4$-alkoxy-carbonyl, di-(C$_1$–C$_6$-alkylamino)-carbonyl, C$_1$–C$_6$-alkylenedioxy, phenyl or phenoxy (which are in each case optionally substituted by fluorine and/or chlorine), R$^2$ represents alkyl, alkenyl, alkinyl or alkoxy which are in each case optionally substituted by cyano or halogen and which in each case have up to 6 carbon atoms, and R$^3$ represents alkyl which is optionally substituted by cyano or halogen and which has from 1 to 6 carbon atoms, represents alkenyl or alkinyl which each case have from 2 to 6 carbon atoms, represents cycloalkyl or cycloalkylalkyl which are in each case optionally substituted by cyano, halogen or C$_1$–C$_4$-alkyl and which in each case have from 3 to 6 carbon atoms in the cycloalkyl moiety and optionally from 1 to 2 carbon atoms in the alkyl moiety, or represents phenyl or phenyl-C$_1$–C$_2$-alkyl which are in each case optionally substituted by cyano, nitro or halogen, or by C$_1$–C$_4$-alkyl, C$_1$–C$_4$-alkoxy, C$_1$–C$_4$-alkylthio, C$_1$–C$_4$-alkylsulphinyl, C$_1$–C$_4$-alkylsulphonyl, di-(C$_1$–C$_4$-alkyl)amino, C$_1$–C$_4$-alkylsulphonylamino, di-(C$_1$–C$_4$-alkyl)aminosulphonyl, C$_1$–C$_4$-alkyl-carbonyl or C$_1$–C$_4$-alkoxy-carbonyl (which are in each case optionally substituted by fluorine and/or chlorine), or, together with R$^2$, represents alkanediyl having 2 to 6 carbon atoms, which comprises reacting a tetrazolinone of the formula

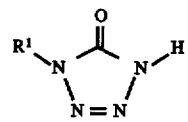  (II)

in which

R$^1$ has the abovementioned meaning, with a carbamoyl halide of the formula

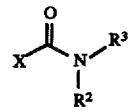  (III)

in which

R$^2$ and R$^3$ have the abovementioned meaning, and

X represents halogen, in the presence of an acid acceptor wherein the acid acceptor is an inorganic or organic base and in the presence of a diluent, at temperatures of between 0° C. and 200° C., and the O-carbamoylation product of the formula (Ia)

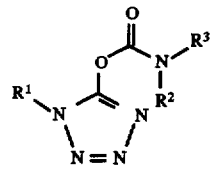  (Ia)

which is formed under these circumstances as a byproduct is either isomerized by heating at the upper range of the above mentioned temperature interval to form the desired product of the formula (I) or is converted by hydrolysis into water-soluble, and thus readily separable, components.

2. The process according to claim 1, wherein

R$^1$ represents alkyl which is optionally substituted by carboxyl, cyano, carbamoyl, halogen, C$_1$–C$_6$-alkoxy, C$_1$–C$_6$-alkylthio, C$_1$–C$_6$-alkylsulphinyl or C$_1$–C$_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, C$_1$–C$_4$-alkyl or C$_1$–C$_4$-alkoxy-carbonyl and which in each case have from 3 to 8 carbon atoms in the cycloalkyl moiety and optionally from 1 to 4 carbon atoms in the alkyl moiety, or represents optionally substituted phenyl, optionally substituted naphthyl, optionally substituted phenyl-C$_1$–C$_4$-alkyl or optionally substituted naphthyl-C$_1$–C$_4$-alkyl, wherein the substituents are carboxyl, cyano, carbamoyl, nitro, amino, hydroxyl or halogen, or C$_1$–C$_4$-alkyl, C$_1$–C$_4$-alkoxy, C$_1$–C$_4$-alkylthio, C$_1$–C$_4$-alkylsulphinyl, C$_1$–C$_4$-alkylsulphonyl, di-(C$_1$–C$_4$-alkyl)amino, C$_1$–C$_4$-alkylsulphonyl-amino, di(C$_1$–C$_4$-alkyl)aminosulphonyl, C$_1$–C$_4$-alkyl-carbonyl, C$_1$–C$_4$-alkylcarbonylamino, C$_1$–C$_4$-alkoxy-carbonyl, di(C$_1$–C$_4$-alkyl-amino)-carbonyl, C$_1$–C$_4$-alkylenedioxy, phenyl or phenoxy (which are in each case optionally substituted by fluorine and/or chlorine), R$^2$ represents alkyl, alkenyl or alkinyl which are in each case optionally substituted by cyano or halogen and which in each case have up to 6 carbon atoms, and R$^3$ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1-C_4$-alkyl and which in each case have from 3 to 6 carbon atoms in the cycloalkyl moiety and optionally from 1 to 2 carbon atoms in the alkyl moiety, or represents phenyl or phenyl-$C_1-C_2$-alkyl which are in each case optionally substituted by cyano, nitro or halogen, or by $C_1-C_4$-alkyl, $C_1-C_4$-alkoxy, $C_1-C_4$-alkylthio, $C_1-C_4$-alkylsulphinyl, $C_1-C_4$-alkylsulphonyl, di-($C_1-C_4$-alkyl)amino, $C_1-C_4$-alkylsulphonylamino, di-($C_1-C_4$-alkyl)aminosulphonyl, $C_1-C_4$-alkyl-carbonyl or $C_1-C_4$-alkoxy-carbonyl (which are in each case optionally substituted by fluorine and/or chlorine), or, together with $R^2$, represents alkanediyl having from 2 to 6 carbon atoms.

3. The process according to claim 1, wherein $R^1$ represents methyl, ethyl, n- or i-propyl, n-, i-, s- or t-butyl, n-, i- or s-pentyl, n-, i- or s-hexyl which are in each case optionally substituted by cyano, fluorine, chlorine, methoxy, ethoxy, methylthio, ethylthio, methylsulphinyl, ethylsulphinyl, methylsulphonyl or ethylsulphonyl, or represents propenyl, butenyl, pentenyl, hexenyl, propinyl, butinyl, pentinyl, or hexinyl which are in each case optionally substituted by cyano, fluorine, chlorine or bromine, or represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, or bromine, or represents phenyl, benzyl, phenylethyl, which are in each case optionally substituted by cyano, fluorine, chlorine or bromine or by methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, dimethylaminosulphonyl, diethylaminosulphonyl, methylcarbonyl, ethylcarbonyl, n- or i-propylcarbonyl, methoxycarbonyl, ethoxycarbonyl, n- or i-propoxycarbonyl, dimethylaminocarbonyl, diethylaminocarbonyl, methylenedioxy or ethylenedioxy (which are in each case optionally substituted by fluorine and/or chlorine), $R^2$ represents methyl, ethyl, n- or i-propyl, n-, i- or s-butyl, propenyl, butenyl, propinyl or butinyl which are in each case optionally substituted by cyano, fluorine or chlorine, and $R^3$ represents methyl, ethyl, n- or i-propyl, n-, i- or s-butyl, propenyl, butenyl, propinyl or butinyl which are in each case optionally substituted by cyano, fluorine or chlorine, represents cyclopropyl, cyctobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, bromine, methyl or ethyl, or represents phenyl, benzyl or phenylethyl which are in each case optionally substituted by cyano, fluorine, chlorine, methyl, ethyl, methoxy or ethoxy.

4. The process according to claim 1 wherein 0.9 to 1.5 mol of carbamoyl halide and 1.0 mol to 1.5 mol of an acid acceptor per mole of tetrazolinone is employed.

5. A process for preparing a substituted N-carbamoyl-tetrazolinone of the formula

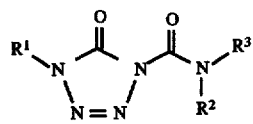

in which $R^1$ represents alkyl which is optionally substituted by carboxyl, cyano, carbamoyl, halogen, $C_1-C_6$-alkoxy, $C_1-C_6$-alkylthio, $C_1-C_6$-alkylsulphinyl or $C_1-C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1-C_4$-alkyl or $C_1-C_4$-alkoxy-carbonyl and which in each case have from 3 to 8 carbon atoms in the cycloalkyl moiety and optionally from 1 to 4 carbon atoms in the alkyl moiety, or represents phenyl, naphthyl, phenyl-$C_1-C_4$-alkyl, naphthyl-$C_1-C_4$-alkyl, furyl, benzofuryl, tetrahydrofuryl, furylmethyl, tetrahydrofurylmethyl, thienyl, benzothienyl, tetrahydrothienyl, thienylmethyl, tetrahydrothienylmethyl, pyrrolyl, indolyl, oxazolyl, benzoxazolyl, oxazolylmethyl, isoxazolyl, isoxazolylmethyl, thiazolyl, benzothiazolyl, thiazolylmethyl, pyrazolyl, oxadiazolyl, oxadiazolylmethyl, thiadiazolyl, thiadiazolylmethyl, triazolyl, pyridyl, quinolinyl, isoquinolinyl, pyridylmethyl, pyrazinyl, pyridazinyl, pyrimidinyl, quinazolinyl, quinoxalinyl, pyrimidinylmethyl, triazinyl or triazinylmethyl which are in each case optionally substituted by carboxyl, cyano, carbamoyl, nitro, amino, hydroxyl or halogen, or by $C_1-C_4$-alkyl, $C_1-C_4$-alkoxy, $C_1-C_4$-alkylthio, $C_1-C_4$-alkylsulphinyl, $C_1-C_4$-alkylsulphonyl, di-($C_1-C_4$-alkyl)amino, $C_1-C_4$-alkylsulphonylamino, di-($C_1-C_4$-alkyl)aminosulphonyl, $C_1-C_4$-alkyl-carbonyl, $C_1-C_4$-alkylcarbonylamino, $C_1-C_4$-alkoxy-carbonyl, di-($C_1-C_4$-alkylamino)-carbonyl, $C_1-C_4$-alkylenedioxy, phenyl or phenoxy (which are in each case optionally substituted by fluorine and/or chlorine), $R^2$ represents alkyl, alkenyl, alkinyl or alkoxy which are in each case optionally substituted by cyano or halogen and which in each case have up to 6 carbon atoms, and $R^3$ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1-C_4$-alkyl and which in each case have from 3 to 6 carbon atoms in the cycloalkyl moiety and optionally from 1 to 2 carbon atoms in the alkyl moiety, or represents phenyl or phenyl-$C_1-C_2$-alkyl which are in each case optionally substituted by cyano, nitro or halogen, or by $C_1-C_4$-alkyl, $C_1-C_4$-alkoxy, $C_1-C_4$-alkylthio, $C_1-C_4$-alkylsulphinyl, $C_1-C_4$-alkylsulphonyl, di-($C_1-C_4$-alkyl)amino, $C_1-C_4$-alkylsulphonylamino, di-($C_1-C_4$-alkyl)aminosulphonyl, $C_1-C_4$-alkyl-carbonyl or $C_1-C_4$-alkoxy-carbonyl (which are in each case optionally substituted by fluorine and/or chlorine), or, together with $R^2$, represents alkanediyl having 2 to 6 carbon atoms, which comprises reacting an optionally isolated metal salt of the formula

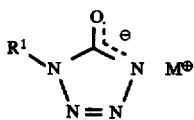

in which
R¹ has the abovementioned meaning, and
M represents an alkali metal equivalent, an alkaline earth metal equivalent or an earth metal equivalent, with a carbamoyl halide of the formula

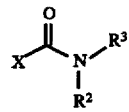

in which
R² and R³ have the abovementioned meaning, and
X represents halogen,
in the presence of a diluent, at temperatures of between 0° C. and 200° C., and the O-carbamoylation product of the formula (Ia)

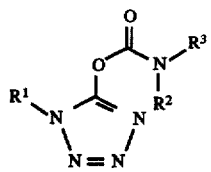

which is formed under these circumstances as a byproduct is either isomerized by heating at the upper range of the above mentioned temperature interval to form the desired product of the formula (I) or is converted by hydrolysis into water-soluble, and thus readily separable, components.

6. The process according to claim 5, wherein
R¹ represents alkyl which is optionally substituted by carboxyl, cyano, carbamoyl, halogen, $C_1$–$C_6$-alkoxy, $C_1$–$C_6$-alkylthio, $C_1$–$C_6$-alkylsulphinyl or $C_1$–$C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1$–$C_4$-alkyl or $C_1$–$C_4$-alkoxy-carbonyl and which in each case have from 3 to 8 carbon atoms in the cycloalkyl moiety and optionally from 1 to 4 carbon atoms in the alkyl moiety, or represents optionally substituted phenyl, optionally substituted naphthyl, optionally substituted phenyl-$C_1$–$C_4$-alkyl or optionally substituted naphthyl-$C_1$–$C_4$-alkyl, wherein the substituents are carboxyl, cyano, carbamoyl, nitro, amino, hydroxyl or halogen, or $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonyl-amino, di($C_1$–$C_4$-alkyl)aminosulphonyl, $C_1$–$C_4$-alkyl-carbonyl, $C_1$–$C_4$-alkylcarbonylamino, $C_1$–$C_4$-alkoxy-carbonyl, di($C_1$–$C_4$-alkyl-amino)-carbonyl, $C_1$–$C_4$-alkylenedioxy, phenyl or phenoxy (which are in each case optionally substituted by fluorine and/or chlorine),
R² represents alkyl, alkenyl or alkinyl which are in each case optionally substituted by cyano or halogen and which in each case have up to 6 carbon atoms, and R³ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1$–$C_4$-alkyl and which in each case have from 3 to 6 carbon atoms in the cycloalkyl moiety and optionally from 1 to 2 carbon atoms in the alkyl moiety, or represents phenyl or phenyl-$C_1$–$C_2$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkyl-sulphonylamino, di-($C_1$–$C_4$-alkyl)aminosulphonyl, $C_1$–$C_4$-alkyl-carbonyl or $C_1$–$C_4$-alkoxy-carbonyl (which are in each case optionally substituted by fluorine and/or chlorine),
or, together with R², represents alkanediyl having from 2 to 6 carbon atoms.

7. The process according to claim 5, wherein
R¹ represents methyl, ethyl, n- or i-propyl, n-, i-, s- or t-butyl, n-, i- or s-pentyl, n-, i- or s-hexyl which are in each case optionally substituted by cyano, fluorine, chlorine, methoxy, ethoxy, methylthio, ethylthio, methylsulphinyl, ethylsulphinyl, methylsulphonyl or ethylsulphonyl, or represents propenyl, butenyl, pentenyl, hexenyl, propinyl, butinyl, pentinyl, or hexinyl which are in each case optionally substituted by cyano, fluorine, chlorine or bromine, or represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, or bromine, or represents phenyl, benzyl, phenylethyl, which are in each case optionally substituted by cyano, fluorine, chlorine or bromine or by methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, dimethylaminosulphonyl, diethylaminosulphonyl, methylcarbonyl, ethylcarbonyl, n- or i-propylcarbonyl, methoxycarbonyl, ethoxycarbonyl, n- or i-propoxycarbonyl, dimethylaminocarbonyl, diethylaminocarbonyl, methylenedioxy or ethylenedioxy (which are in each case optionally substituted by fluorine and/or chlorine),
R² represents methyl, ethyl, n- or i-propyl, n-, i- or s-butyl, propenyl, butenyl, propinyl or butinyl which are in each case optionally substituted by cyano, fluorine or chlorine, and
R³ represents methyl, ethyl, n- or i-propyl, n-, i- or s-butyl, propenyl, butenyl, propinyl or butinyl which are in each case optionally substituted by cyano, fluorine or chlorine, represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, bromine, methyl or ethyl, or represents phenyl, benzyl or phenylethyl which are in each case optionally substituted by cyano, fluorine, chlorine, methyl, ethyl, methoxy or ethoxy.

8. The process according to claim 5, wherein 0.9 to 1.5 mols of the carbamoyl halide per mole of the tetrazolinone salt is used.

9. A process for preparing a substituted N-carbamoyl-tetrazolinone of the formula

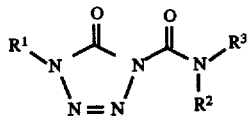
(I)

in which
- R¹ represents alkyl which is optionally substituted by carboxyl, cyano, carbamoyl, halogen, $C_1$–$C_6$-alkoxy, $C_1$–$C_6$-alkylthio, $C_1$–$C_6$-alkylsulphinyl or $C_1$–$C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1$–$C_4$-alkyl or $C_1$–$C_4$-alkoxy-carbonyl and which in each case have from 3 to 8 carbon atoms in the cycloalkyl moiety and optionally from 1 to 4 carbon atoms in the alkyl moiety, or represents phenyl, naphthyl, phenyl-$C_1$–$C_4$-alkyl, naphthyl-$C_1$–$C_4$-alkyl, furyl, benzofuryl, tetrahydrofuryl, furylmethyl, tetrahydrofurylmethyl, thienyl, benzothienyl, tetrahydrothienyl, thienylmethyl, tetrahydrothienylmethyl, pyrrolyl, indolyl, oxazolyl, benzoxazolyl, oxazolylmethyl, isoxazolyl, isoxazolylmethyl, thiazolyl, benzothiazolyl, thiazolylmethyl, pyrazolyl, oxadiazolyl, oxadiazolylmethyl, thiadiazolyl, thiadiazolylmethyl, triazolyl, pyridyl, quinolinyl, isoquinolinyl, pyridylmethyl, pyrazinyl, pyridazinyl, pyrimidinyl, quinazolinyl, quinoxalinyl, pyrimidinylmethyl, triazinyl or triazinylmethyl which are in each case optionally substituted by carboxyl, cyano, carbamoyl, nitro, amino, hydroxyl or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl, $C_1$–$C_4$-alkyl-carbonylamino, $C_1$–$C_4$-alkoxy-carbonyl, di-($C_1$–$C_4$-alkylamino)-carbonyl, $C_1$–$C_4$-alkylenedioxy, phenyl or phenoxy (which are in each case optionally substituted by fluorine and/or chlorine),
- R² represents alkyl, alkenyl, alkinyl or alkoxy which are in each case optionally substituted by cyano or halogen and which in each case have up to 6 carbon atoms, and
- R³ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1$–$C_4$-alkyl and which in each case have from 3 to 6 carbon atoms in the cycloalkyl moiety and optionally from 1 to 2 carbon atoms in the alkyl moiety, or represents phenyl or phenyl-$C_1$–$C_2$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl or $C_1$–$C_4$-alkoxy-carbonyl (which are in each case optionally substituted by fluorine and/or chlorine),
- or, together with R², represents alkanediyl having 2 to 6 carbon atoms, which comprises isomerizing a substituted carbamoyloxytetrazole of the formula

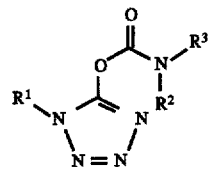
(Ia)

in which
R¹, R² and R³ have the abovementioned meanings,
wherein compounds of the formula I are optionally present, to form the corresponding N-carbamoyl-tetrazolinones of the formula (I), where appropriate in the presence of a diluent and where appropriate in the presence of a reaction auxiliary wherein said reaction auxiliary is a basic organic nitrogen compound, iodine or an alkali metal iodide, at temperatures of between 50° C. and 200° C.

10. The process according to claim 9, wherein
- R¹ represents alkyl which is optionally substituted by carboxyl, cyano, carbamoyl, halogen, $C_1$–$C_6$-alkoxy, $C_1$–$C_6$-alkylthio, $C_1$–$C_6$-alkylsulphinyl or $C_1$–$C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1$–$C_4$-alkyl or $C_1$–$C_4$-alkoxy-carbonyl and which in each case have from 3 to 8 carbon atoms in the cycloalkyl moiety and optionally from 1 to 4 carbon atoms in the alkyl moiety, or represents optionally substituted phenyl, optionally substituted naphthyl, optionally substituted phenyl-$C_1$–$C_4$-alkyl or optionally substituted naphthyl-$C_1$–$C_4$-alkyl, wherein the substituents are carboxyl, cyano, carbamoyl, nitro, amino, hydroxyl or halogen, or $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonyl-amino, di($C_1$–$C_4$-alkyl)aminosulphonyl, $C_1$–$C_4$-alkyl-carbonyl, $C_1$–$C_4$-alkylcarbonylamino, $C_1$–$C_4$-alkoxy-carbonyl, di($C_1$–$C_4$-alkyl-amino)-carbonyl, $C_1$–$C_4$-alkylenedioxy, phenyl or phenoxy (which are in each case optionally substituted by fluorine and/or chlorine),
- R² represents alkyl, alkenyl or alkinyl which are in each case optionally substituted by cyano or halogen and which in each case have up to 6 carbon atoms, and
- R³ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1$–$C_4$-alkyl and which in each case have from 3 to 6 carbon atoms in the cycloalkyl moiety and optionally from 1 to 2 carbon atoms in the alkyl moiety, or represents phenyl or phenyl-$C_1$–$C_4$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl or $C_1$–$C_4$alkoxy-carbonyl (which are in each case optionally substituted by fluorine and/or chlorine), or, together with R², represents alkanediyl having from 2 to 6 carbon atoms.

11. The process according to claim 9, wherein

R¹ represents methyl, ethyl, n- or i-propyl, n-, i-, s- or t-butyl, n-, i- or s-pentyl, n-, i- or s-hexyl which are in each case optionally substituted by cyano, fluorine, chlorine, methoxy, ethoxy, methylthio, ethylthio, methylsulphinyl, ethylsulphinyl, methylsulphonyl or ethylsulphonyl, or represents propenyl, butenyl, pentenyl, hexenyl, propinyl, butinyl, pentinyl, or hexinyl which are in each case optionally substituted by cyano, fluorine, chlorine or bromine, or represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, or bromine, or represents phenyl, benzyl, phenylethyl, which are in each case optionally substituted by cyano, fluorine, chlorine or bromine or by methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, dimethylaminosulphonyl, diethylaminosulphonyl, methylcarbonyl, ethylcarbonyl, n- or i-propylcarbonyl, methoxycarbonyl, ethoxycarbonyl, n- or i-propoxycarbonyl, dimethylaminocarbonyl, diethylaminocarbonyl, methylenedioxy or ethylenedioxy (which are in each case optionally substituted by fluorine and/or chloride), R² represents methyl, ethyl, n- or i-propyl, n-, i- or s-butyl, propenyl, butenyl, propinyl or butinyl which are in each case optionally substituted by cyano, fluorine or chlorine, and R³ represents methyl, ethyl, n- or i-propyl, n-, i- or s-butyl, propenyl, butenyl, propinyl or butinyl which are in each case optionally substituted by cyano, fluorine or chlorine, represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, bromine, methyl or ethyl, or represents phenyl, benzyl or phenylethyl which are in each case optionally substituted by cyano, fluorine, chlorine, methyl, ethyl, methoxy or ethoxy.

12. A process for preparing a substituted N-carbamoyl-tetrazolinone of the formula

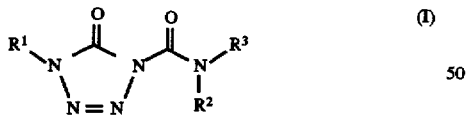

(I)

in which

R¹ represents alkyl which is optionally substituted by carboxyl, cyano, carbamoyl, halogen, $C_1$–$C_6$-alkoxy, $C_1$–$C_6$-alkylthio, $C_1$–$C_6$-alkylsulphinyl or $C_1$–$C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1$–$C_4$-alkyl or $C_1$–$C_4$-alkoxy-carbonyl and which in each case have from 3 to 8 carbon atoms in the cycloalkyl moiety and optionally from 1 to 4 carbon atoms in the alkyl moiety, or represents phenyl, naphthyl, phenyl-$C_1$–$C_4$-alkyl, naphthyl-$C_1$–$C_4$-alkyl, furyl, benzofuryl, tetrahydrofuryl, furylmethyl, tetrahydrofurylmethyl, thienyl, benzothienyl, tetrahydrothienyl, thienylmethyl, tetrahydrothienylmethyl, pyrrolyl, indolyl, oxazolyl, benzoxazolyl, oxazolylmethyl, isoxazolyl, isoxazolylmethyl, thiazolyl, benzothiazolyl, thiazolylmethyl, pyrazolyl, oxadiazolyl, oxadiazolylmethyl, thiadiazolyl, thiadiazolylmethyl, triazolyl, pyridyl, quinolinyl, isoquinolinyl, pyridylmethyl, pyrazinyl, pyridazinyl, pyrimidinyl, quinazolinyl, quinoxalinyl, pyrimidinylmethyl, triazinyl or triazinylmethyl which are in each case optionally substituted by carboxyl, cyano, carbamoyl, nitro, amino, hydroxyl or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl, $C_1$–$C_4$-alkyl-carbonylamino, $C_1$–$C_4$-alkoxy-carbonyl, di-($C_1$–$C_4$-alkylamino)-carbonyl, $C_1$–$C_4$-alkylenedioxy, phenyl or phenoxy (which are in each case optionally substituted by fluorine and/or chlorine), R² represents alkyl, alkenyl, alkinyl or alkoxy which are in each case optionally substituted by cyano or halogen and which in each case have up to 6 carbon atoms, and R³ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1$–$C_4$-alkyl and which in each case have from 3 to 6 carbon atoms in the cycloalkyl moiety and optionally from 1 to 2 carbon atoms in the alkyl moiety, or represents phenyl or phenyl-$C_1$–$C_4$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl or $C_1$–$C_4$-alkoxy-carbonyl (which are in each case optionally substituted by fluorine and/or chlorine), or, together with R², represents alkanediyl having 2 to 6 carbon atoms, which comprises reacting a substituted carbamoyloxytetrazole of the formula

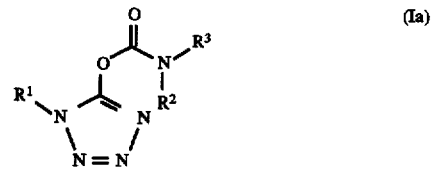

(Ia)

in which

R¹, R² and R³ have the abovementioned meanings, with water and/or an alcohol, optionally in the presence of an inert organic solvent and where appropriate in the presence of a reaction auxiliary wherein said reaction auxiliary is a basic organic nitrogen compound, iodine, or an alkali metal iodide at temperatures of between 10° C. and 150° C., and the products of the hydrolysis or the alcoholysis of the compounds of the formula (Ia) are separated off.

13. The process according to claim 12, wherein

R¹ represents alkyl which is optionally substituted by carboxyl, cyano, carbamoyl, halogen, $C_1$–$C_6$-alkoxy, $C_1$–$C_6$-alkylthio, $C_1$–$C_6$-alkylsulphinyl or $C_1$–$C_6$-alkylsulphonyl and which has from 1 to 10 carbon atoms, represents alkenyl or alkinyl which are in each case optionally substituted by carboxyl, cyano, carbamoyl or halogen and which in each case have from 2 to 10 carbon atoms, represents cycloalkyl or cycloalkylalkyl which are in each case optionally substituted by carboxyl, cyano, carbamoyl, halogen, $C_1$–$C_4$-alkyl or $C_1$–$C_4$-alkoxy-carbonyl and which in each case have from 3 to 8 carbon atoms in the cycloalkyl moiety and optionally from 1 to 4 carbon atoms in the alkyl moiety, or represents optionally substituted phenyl, optionally substituted naphthyl, optionally substituted phenyl-$C_1$–$C_4$-alkyl or optionally substituted naphthyl-$C_1$–$C_4$-alkyl, wherein the substituents are carboxyl, cyano, carbamoyl, nitro, amino, hydroxyl or halogen, or $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonyl-amino, di($C_1$–$C_4$-alkyl)aminosulphonyl, $C_1$–$C_4$-alkyl-carbonyl, $C_1$–$C_4$-alkylcarbonylamino, $C_1$–$C_4$-alkoxy-carbonyl, di($C_1$–$C_4$-alkyl-amino)-carbonyl, $C_1$–$C_4$-alkylenedioxy, phenyl or phenoxy (which are in each case optionally substituted by fluorine and/or chlorine), $R^2$ represents alkyl, alkenyl or alkinyl which are in each case optionally substituted by cyano or halogen and which in each case have up to 6 carbon atoms, and $R^3$ represents alkyl which is optionally substituted by cyano or halogen and which has from 1 to 6 carbon atoms, represents alkenyl or alkinyl which are in each case optionally substituted by cyano or halogen and which in each case have from 2 to 6 carbon atoms, represents cycloalkyl or cycloalkylalkyl which are in each case optionally substituted by cyano, halogen or $C_1$–$C_4$-alkyl and which in each case have from 3 to 6 carbon atoms in the cycloalkyl moiety and optionally from 1 to 2 carbon atoms in the alkyl moiety, or represents phenyl or phenyl-$C_1$–$C_2$-alkyl which are in each case optionally substituted by cyano, nitro or halogen, or by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)amino, $C_1$–$C_4$-alkylsulphonylamino, di-($C_1$–$C_4$-alkyl)aminosulphonyl, $C_1$–$C_4$-alkyl-carbonyl or $C_1$–$C_4$-alkoxy-carbonyl (which are in each case optionally substituted by fluorine and/or chlorine), or, together with $R^2$, represents alkanediyl having from 2 to 6 carbon atoms.

14. The process according to claim 12, wherein $R^1$ represents methyl, ethyl, n- or i-propyl, n-, i-, s- or t-butyl, n-, i- or s-pentyl, n-, i- or s-hexyl which are in each case optionally substituted by cyano, fluorine, chlorine, methoxy, ethoxy, methylthio, ethylthio, methylsulphinyl, ethylsulphinyl, methylsulphonyl or ethylsulphonyl, or represents propenyl, butenyl, pentenyl, hexenyl, propinyl, butinyl, pentinyl, or hexinyl which are in each case optionally substituted by cyano, fluorine, chlorine or bromine, or represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, or bromine, or represents phenyl, benzyl, phenylethyl, which are in each case optionally substituted by cyano, fluorine, chlorine or bromine or by methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, dimethylaminosulphonyl, diethylaminosulphonyl, methylcarbonyl, ethylcarbonyl, n- or i-propylcarbonyl, methoxycarbonyl, ethoxycarbonyl, n- or i-propoxycarbonyl, dimethylaminocarbonyl, diethylaminocarbonyl, methylenedioxy or ethylenedioxy (which are in each case optionally substituted by fluorine and/or chlorine), $R^2$ represents methyl, ethyl, n- or i-propyl, n-, i- or s-butyl, propenyl, butenyl, propinyl or butinyl which are in each case optionally substituted by cyano, fluorine or chlorine, and $R^3$ represents methyl, ethyl, n- or i-propyl, n-, i- or s-butyl, propenyl, butenyl, propinyl or butinyl which are in each case optionally substituted by cyano, fluorine or chlorine, represents cyclopropyl, cyclobutyl, cyclopentyl, cyclohexyl, cyclopropylmethyl, cyclobutylmethyl, cyclopentylmethyl or cyclohexylmethyl which are in each case optionally substituted by cyano, fluorine, chlorine, bromine, methyl or ethyl, or represents phenyl, benzyl or phenylethyl which are in each case optionally substituted by cyano, fluorine, chlorine, methyl, ethyl, methoxy or ethoxy.

* * * * *

UNITED STATES PATENT AND TRADEMARK OFFICE
CERTIFICATE OF CORRECTION

PATENT NO. : 5,686,392
DATED : November 11, 1997
INVENTOR(S) : Stelzer, et al.

It is certified that error appears in the above-indentified patent and that said Letters Patent is hereby corrected as shown below:

Col. 15, lines 42-43  Delete " di-$(C_1-C_6$-alkylamino)-carbonyl, $C_1-C_6$-alkylenedioxy, " and substitute -- di-$(C_1-C_4$-alkylamino)-carbonyl, $C_1-C_4$-alkylenedioxy --

Col. 24, line 35  Delete " phenyl-$C_1-C_4$-alkyl " and substitute -- phenyl-$C_1-C_2$-alkyl --

Signed and Sealed this

Fifteenth Day of September, 1998

Attest:

BRUCE LEHMAN

Attesting Officer

Commissioner of Patents and Trademarks